United States Patent [19]

Bertus et al.

[11] 4,039,476
[45] Aug. 2, 1977

[54] OXIDATIVE DEHYDROGENATION CATALYSTS

[75] Inventors: Brent J. Bertus; Donald C. Tabler; Marvin M. Johnson, all of Bartlesville, Okla.

[73] Assignee: Phillips Petroleum Company, Bartlesville, Okla.

[21] Appl. No.: 582,571

[22] Filed: May 30, 1975

Related U.S. Application Data

[62] Division of Ser. No. 381,552, July 23, 1973, Pat. No. 3,894,056.

[51] Int. Cl.$^2$ ............................................. B01J 27/14
[52] U.S. Cl. ....................................... 252/437; 252/435
[58] Field of Search ................................. 252/435, 437

[56] References Cited

U.S. PATENT DOCUMENTS

| | | | |
|---|---|---|---|
| 2,625,519 | 1/1953 | Hartig | 252/437 X |
| 3,228,966 | 1/1966 | Adams | 252/437 X |
| 3,755,196 | 8/1973 | Mickelson | 252/435 |
| 3,840,472 | 10/1974 | Colgan et al. | 252/435 |
| 3,894,056 | 7/1975 | Bertus et al. | 252/435 X |

*Primary Examiner*—Patrick P. Garvin
*Assistant Examiner*—William G. Wright

[57] ABSTRACT

Alkenes and/or alkadienes are contacted with molecular oxygen and an oxidative dehydrogenation catalyst consisting essentially of phosphorus, molybdenum, cobalt and oxygen, wherein the atom ratio of phosphorus to molybdenum is in the range of about 0.5:1 to about 5:1 and the atom ratio of cobalt to molybdenum is in the range of about 0.1:1 to about 3:1, to produce furan compounds.

21 Claims, No Drawings

OXIDATIVE DEHYDROGENATION CATALYSTS

This is a division of copending application Ser. No. 381,552, filed July 23, 1973, now U.S. Pat. No. 3,894,056.

This invention relates to oxidative dehydrogenation catalysts and the use thereof for the conversion of alkenes and/or alkadienes to furan compounds.

Furan compounds can react readily with oxygen under oxidation conditions to produce ring cleavage and the formation of polymers. Accordingly, the production of furan compounds by the oxidative dehydrogenation of hydrocarbons has generally been avoided. Recently it has been discovered that furan compounds can be produced by the oxidative dehydrogenation of hydrocarbons in the presence of certain specific catalysts without substantial conversion of the furan compounds to undesirable products. The search for additional catalyst suitable for this reaction continues.

Accordingly, it is an object of the present invention to provide a new and improved oxidative dehydrogenation catalyst. Another object of the invention is to provide a new and improved process for the conversion of alkenes or alkadienes to furan compounds. Other objects, aspects and advantages of the invention will be apparent to those skilled in the art.

In accordance with the present invention there is provided an improved catalyst for the production of furan type compounds from alkenes and alkadienes having from 4 to 10 carbon atoms, which catalyst consists essentially of molybdenum, cobalt, phosphorus and oxygen, with the atom ratio of phosphorus to molybdenum being in the range of about 0.5:1 to about 5:1, preferably in the range of about 1:1 to about 4:1, and the atom ratio of cobalt to molybdenum being in the range of about 0.1:1 to about 3:1, preferably in the range of about 0.2:1 to about 2:1.

If desired, these catalysts can be supported on conventional solid catalytic support materials, for example zinc oxide, silica, alumina, boria, magnesia, titania, zirconia, and mixtures thereof. Where a catalyst support is employed, the support will generally constitute from about 10 to about 98, preferably from about 75 to about 95, weight percent of the total catalyst composition. Supports having a surface area in the range of about 2 to about 50 m²/g, preferably in the range of about 5 to about 20 m²/g, are desirable.

The catalysts of the present invention can be prepared by many suitable techniques, for example coprecipitation, impregnation, in exchange, aqueous or nonaqueous solution or suspension mixing, or dry mixing. In general, any method can be employed which will provide a composition containing the desired elements in the defined proportions, and which has a catalytic surface area in the range of about 0.05 to about 20 m²/g, preferably in the range of about 0.1 to about 5 m²/g. Thus, the catalyst components and/or compounds thereof can be combined in any suitable manner. In a presently preferred embodiment, the catalyst is preferably a composition such as that prepared by dry mixing ammonium diacid phosphate, cobalt nitrate, and ammonium molybdate followed by calcination. Any compound of molybdenum, cobalt or phosphorus can be employed in the preparation of the catalyst so long as none of the compounds are detrimental to the final oxidative dehydrogenation catalyst and essentially all of the elements in the compounds employed, other than the molybdenum, cobalt, phosphorus, and oxygen, are removed from the final catalyst by washing or by volatilization. However, small or trace amounts of some other elements which can be involved in the preparation of the catalyst can be tolerated in the final catalytic composition. For example, if alkali metal or alkaline earth metal hydroxides are employed in the preparation of the catalyst, very small residual amounts of such alkali metal and alkaline earth metals are not detrimental. Similarly, if cobalt sulfate is employed in the preparation of the catalyst, small residual amounts of sulfur can be tolerated.

Generally, however, the preferred cobalt and molybdenum compounds are the oxides or phosphates of these elements or compounds which are converted to the oxide or phosphate on calcination. Thus, suitable components include the oxides, nitrates, halides, sulfates, oxalates, acetates, carbonates, propionates, tartrates, hydroxides, ammonium salts, and the like. Examples of these compounds include cobalt nitrate, cobalt acetate, cobalt sulfate, cobalt hydroxide, cobalt oxide, cobalt propionate, cobalt phosphate, molybdenum oxide, ammonium molybdate, molybdenum phosphate and the like. Preferred phosphorus compounds include the phosphoric acids, phosphorus pentoxide, cobalt phosphate, diammonium hydrogen phosphate and other ammonium phosphates, and the like. The term "phosphate" includes not only the monophosphate ion, $PO_4^{-3}$, but also polyphosphate ions $(P_nO_{3n+1})^{-(n+2)}$ and $[P_nO_{3n-1}(OH)_2]^{-n}$ in which $n$ is an integer in the range of 2 through 100.

One technique for forming an unsupported catalyst of the present invention comprises mixing one or more phosphorus compounds, one or more molybdenum compounds, and one or more cobalt compounds. The compounds can be admixed in the form of the dry compounds and then calcined, or they can be admixed in the presence of a suitable diluent, for example water, to form a paste. The paste can be dried, if desired, before calcining. The catalyst formation can be completed by calcining the dried solids. A particle forming step such as pelletizing or screening can precede the drying step or the calcining step.

A technique for forming a supported catalyst of the present invention comprises sequentially impregnating the support with solutions or dispersions of each component compound, drying and calcining the impregnated support.

The calcining step will be accomplished under conditions which ensure the conversion of any nonoxide or nonphosphate compounds to the oxide or phosphate form and the volatilizing of any undesired elements. In general, the calcining step comprises heating the catalyst composition to a temperature in the range of about 800° F to about 1500° F for a time in the range of about 1 to about 40 hours. Presently preferred calcining conditions comprise a temperature in the range of about 850° F to about 1400° F for a time in the range of about 2 to about 24 hours in the presence of a molecular oxygen-containing gas, for example, air.

Suitable feeds for conversion to furan compounds include the unsaturated acyclic hydrocarbons, particularly the acyclic alkenes and acyclic alkadienes having from 4 to 10 carbon atoms. Examples include butene-1, butene-2, pentene-1, isopentene, hexene-1, heptene-2, octene-1, decene-1, 2-methylbutene-1, hexene-3,2-ethylbutene-1, 2-methylpentene-3, 3-ethylhexene-2, butadiene-1,3, pentadiene-1,3, isoprene, hexadiene-1,3, decadiene-1,3, and the like, and mixtures thereof. The acyclic alkadienes having from 4 to 5 carbon atoms are presently preferred.

The furan compounds produced by the process of the present invention have the formula

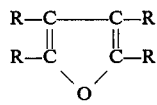

wherein each R is individually selected from the group consisting of hydrogen and alkyl radicals having from 1 to 6 carbon atoms, the total carbon atoms in the R radicals being in the range of 0 to 6. Representative products include furan, 2-methylfuran, 3-methylfuran, 2,5-diethylfuran, 2-n-hexylfuran, 2-isopropyl-3-methylfuran, 3,4-n-dipropylfuran, 3-methyl-4-n-butylfuran and the like.

In accordance with the present invention, a hydrocarbon feed comprising one or more acyclic alkenes and/or one or more acyclic alkadienes is contacted, under suitable reaction conditions for conversion to furan compounds, with a molecular oxygen-containing gas in the presence of the hereinabove defined catalyst. The molecular oxygen-containing gas can be high purity oxygen, oxygen diluted with an inert diluent such as nitrogen, flue gas containing residual oxygen, air, or any other source of molecular oxygen which is at least essentially free of contaminants which would be detrimental to the desired reaction. In a presently preferred embodiment, the oxidative dehydrogenation process is carried out in the absence of any halogen. In general, the temperature will be in the range of about 800° F to about 1200° F, and preferably will be in the range of about 900° F to about 1100° F. Any suitable pressure can be employed, but in general the pressure will be in the range of about 0.05 to about 250 psig, and preferably will be in the range of about 0.1 to about 25 psig. The hydrocarbon feed rate will generally be in the range of about 10 to about 1,000 standard cubic feet of alkenes and/or alkadienes per hour per cubic foot of catalyst bed (GHSV), and preferably will be in the range of about 100 to about 500 GHSV. The mol ratio of molecular oxygen to alkenes and alkadienes will generally be in the range of about 0.1:1 to about 3:1, and preferably will be in the range of about 0.5:1 to about 2:1. Steam can be employed in the reaction zone as a diluent and heat transfer agent. When steam is utilized, the mol ratio of steam to alkenes and alkadienes will generally be in the range of about 0.1:1 to about 50:1, and preferably will be in the range of about 5:1 to about 30:1.

The alkenes, if present, are largely converted to the corresponding alkadienes. The alkadienes, in turn, are converted in significant quantities to the corresponding furan compounds. However, the reaction effluent can also contain unreacted feed material, alkenes including ethylene, propylene, and butenes, water, oxides of carbon, alkenylcycloolefins, crotonaldehyde, acetaldehyde and other oxygenated products. The furam compounds can be recovered by suitable techniques, for example by condensation from the reactor gas effluent followed by distillation. Unconverted alkenes and/or alkadienes can be recovered and recycled to the reactor, as can other materials such as crotonaldehyde which are convertible to furan compounds under the reaction conditions. If desired, the conversion of alkenes to furan compounds can be conducted in two reaction zones in series. The first reaction zone can be operated under conditions favorable for the converson of the alkenes to alkadienes, while the second reaction zone can be operated under conditions favorable to the conversion of the alkadienes to furan compounds. The effluent from the first reaction zone can be subjected to conventional separation techniques to recover unconverted alkenes for recycle to the first reaction zone and a concentrated alkadiene stream for feed to the second reaction zone. If desired, the total effluent from the first reaction zone can be passed directly to the second reaction zone without separation. The effluent of the second reaction zone can be processed for recovery and recycle of unreacted alkadienes to the secton reaction zone and for recovery of a furan compound product. The catalyst of the present invention can be employed in both reaction zones, or another suitable dehydrogenation catalyst can be employed in the first reaction zone while the present catalyst is utilized in the second reaction zone.

The following example is presented in further illustration of the invention and should not be construed in undue limitation thereof.

EXAMPLE

Small lots of catalyst were prepared utilizing sufficient quantities of each ingredient to obtain the atom ratios shown in the Table. About two cubic centimeters of catalyst was used in each run. The catalysts were normally tested at reactor temperatures of 700°, 800°, 900°and 1000° F in sequence. Data are reported only for those runs in which significant amounts of furan were produced.

Test conditions included 400 GHSV butadiene, 400 GHSV oxygen (air source) and 8000 GHSV steam.

Table

| Run No. | P/Mo Atom Ratio | Co/Mo Atom Ratio | Reactor Temp. °F | Butadiene Conversion % | Yield Mol % Furan | Selectivities % Furan |
|---|---|---|---|---|---|---|
| 1 | — | 0.6/1 | 700 | 0.1 | 0 | 0 |
| 2 | — | " | 800 | 14.0 | 0 | 0 |
| 3 | — | " | 900 | 26.0 | 0 | 0 |
| 4 | — | " | 1000 | 29.3 | 0 | 0 |
| 5 | 0.06/1 | 0.19/1 | 700 | 20.0 | 1.16 | 5.8 |
| 6 | 10/1 | 0.56/1 | 1000 | 12.0 | 2.4 | 19.5 |
| 7 | 1.4/1 | 1.5/1 | 800 | 10.6 | 5.0 | 47.2 |
| 8 | " | " | 900 | 20.0 | 14.5 | 72.5 |
| 9 | " | " | 1000 | 27.1 | 15.1 | 55.6 |
| 10 | 3.1/1 | 1.9/1 | 800 | 11.7 | 4.2 | 35.9 |
| 11 | " | " | 900 | 23.4 | 14.6 | 62.4 |
| 12 | " | " | 1000 | 22.0 | 13.1 | 59.5 |
| 13 | 3.2/1 | 1.95/1 | 900 | 4.5 | 2.8 | 62.0 |
| 14 | " | " | 1000 | 11.7 | 6.7 | 57.1 |
| 15 | 3.2/1 | 1.95/1 | 900 | 5.3 | 3.2 | 60.7 |
| 16 | " | " | 1000 | 15.8 | 8.9 | 56.1 |
| 17 | 2.8/1 | 1.96/1 | 900 | 20.0 | 10.6 | 53.0 |
| 18 | " | " | 1000 | 31.0 | 13.6 | 43.8 |
| 19 | " | " | 900 | 7.3 | 4.9 | 66.8 |
| 20 | " | " | 1000 | 25.1 | 13.8 | 55.1 |
| 21 | 3.2/1 | " | 900 | 9.7 | 5.3 | 54.4 |
| 22 | " | " | 900 | 4.8 | 2.8 | 57.8 |
| 23 | " | " | 1000 | 19.5 | 11.2 | 57.4 |
| 24 | 3.1/1 | 1.9/1 | 900 | 4.9 | 2.3 | 48.0 |

The catalyst of runs 1-4 consisted of 8.5 wt % MoO₃ and 2.5 wt % CoO supported on 89.0 wt % alumina. It was calcined at 1000° F for 17 hours.

The catalyst of run 5 was prepared by impregnating the catalyst of runs 1-4 with phosphomolybdic acid. It was dried and calcined at 1000° F for 17 hours. The catalyst of run 6 was prepared by impregnating the catalyst of runs 1-4 with phosphoric acid (H₃PO₄). It was dried and calcined at 1000° F for 17 hours. The catalyst of runs 7-9 was prepared by mixing together the dry salts of cobalt acetate, ammonium molybdate and ammoium dihydrogen phosphate. It was calcined at 1200° F for 15 hours.

The catalyst of runs 10–12 was prepared and calcined in a manner similar to the catalyst of runs 7–9.

The catalyst of runs 13–14 was prepared like the catalyst of runs 7–9 except that it was calcined at 1200° F for 23 hours.

The catalyst of runs 15–16 was prepared by mixing together the salts used in runs 7–9 except sufficient water was added to form a paste. After drying it was calcined at 1200° F for 23 hours.

The catalyst of runs 17–18 was prepared by mixing together a paste comprising cobalt acetate, ammonium molybdate, diammonium hydrogen phosphate and water. After drying the product was calcined at 100° F for 8 hours.

The catalyst of runs 19–20 was prepared from the catalyst of runs 17–18 by recalcining that catalyst at 1200° F for 18 hours.

The catalyst of run 21 was prepared by mixing together a paste comprising cobalt acetate, ammonium molybdate, ammonium dihydrogen phosphate and water. After drying it was calcined at 1000° F for 8 hours.

The catalyst of runs 22–23 was prepared from the catalyst of run 21 by recalcining the catalyst at 1200° F for 18 hours.

The catalyst of run 24 was spent catalyst from runs 10–12, recalcined at 1200° F for 18 hours.

The gaseous effluents from each run, on a dry basis, were analyzed by means of gas-liquid chromatography. Products found included unreacted butadiene, furan, acetaldehyde, carbon oxides, ethylene, propylene and butenes. The reported selectivity to furan is a modified selectivity based on the above gaseous product analyses. The yields of furan are in terms of mols per 100 mols of butadiene feedstock.

The data show that significant quantities of furan are produced when the reactor temperature is about 800° F or higher under the process conditions used, with 1000° F being generally preferable over the lower temperatures.

Results from run 24 indicate that calcining spent catalyst again is not sufficient to reactivate it.

The best results were obtained when the overall Mo/Co/P atom ratios of the catalysts tested were in the range of 1/1.5/1.4 to about 1/2/3.1.

Reasonable variations and modifications are possible within the scope of the foregoing disclosure and the appended claims to the invention.

That which is claimed:

1. A composition consisting essentially of molybdenum, cobalt, phosphorus, and oxygen, with an atom ratio of phosphorus to molybdenum in the range of about 1.4:1 to about 4:1 and an atom ratio of cobalt to molybdenum in the range of about 1.5:1 to about 3:1.

2. An oxidative dehydrogenation catalyst consisting essentially of a composition in accordance with claim 1 wherein about 10 to about 98 weight percent of said catalyst is a solid catalyst support material.

3. An oxidative dehydrogenation catalyst in accordance with claim 2 wherein said solid catalyst support material has a surface area in the range of about 2 to about 50 m$^2$/g.

4. An oxidative dehydrogenation catalyst in accordance with claim 3 wherein said solid catalyst support material constitutes from about 75 to about 95 weight percent of said catalyst.

5. An oxidative dehydrogenation catalyst in accordance with claim 4 wherein said catalyst has a surface area in the range of about 0.05 to about 20 m$^2$/g.

6. An oxidative dehydrogenation catalyst in accordance with claim 5 wherein the Mo/Co/P atom ratio is in the range of about 1/1.5/1.4 to about 1/1.9/3.1.

7. A composition in accordance with claim 1 wherein said atom ratio of cobalt to molybdenum is in the range of about 1.5:1 to about 2:1.

8. A composition in accordance with claim 7 wherein said atom ratio of phosphorus to molybdenum is in the range of about 1.4:1 to about 3.2:1.

9. A composition in accordance with claim 7 wherein said atom ratio of phosphorus to molybdenum is in the range of abbout 1.4:1 to about 3.1:1.

10. A composition in accordance with claim 15 wherein said atom ratio of cobalt to molybdenum is in the range of about 1.5:1 to about 1.9:1.

11. A composition in accordance with claim 7 wherein said atom ratio of cobalt to molybdenum is in the range of about 1.5:1 to about 1.9:1.

12. A composition in accordance with claim 1 wherein said atom ratio of phosphorus to molybdenum is in the range of about 1.4:1 to about 3.2:1.

13. A composition in accordance with claim 1 wherein said atom ratio of phosphorus to molybdenum is in the range of about 1.4:1 to 3.1:1.

14. An unsupported calcined composition consisting of molybdenum, cobalt, phosphorus, and oxygen, with an atom ratio of phosphorus to molybdenum in the range of about 1.4:1 to about 4:1 and an atom ratio of cobalt to molybdenum in the range of about 1.5:1 to about 3:1.

15. A composition in accordance with claim 14 wherein said atom ratio of cobalt to molybdenum is in the range of about 1.5:1 to about 2:1.

16. A composition in accordance with claim 15 wherein said atom ratio of phosphorus to molybdenum is in the range of about 1.4:1 to about 3.2:1.

17. A composition in accordance with claim 15 wherein said atom ratio of phosphorus to molybdenum is in the range of about 1.4:1 to about 3.1:1.

18. A composition in accordance with claim 17 wherein said atom ratio of cobalt to molybdenum is in the range of about 1.5:1 to about 1.9:1.

19. A composition in accordance with claim 15 wherein said atom ratio of cobalt to molybdenum is in the range of about 1.5:1 to about 1.9:1.

20. A composition in accordance with claim 14 wherein said atom ratio of phosphorus to molybdenum is in the range of about 1.4 to about 3.2:1.

21. A composition in accordance with claim 14 wherein said atom ratio of phosphorus to molybdenum is in the range of about 1.4 to about 3.1:1.

* * * * *

UNITED STATES PATENT AND TRADEMARK OFFICE
CERTIFICATE OF CORRECTION

PATENT NO. : 4,039,476

DATED : August 2, 1977

INVENTOR(S) : Brent J. Bertus; Donald C. Tabler; Marvin M. Johnson

It is certified that error appears in the above-identified patent and that said Letters Patent are hereby corrected as shown below:

Column 6, line 33, after "to" and before "3.1:1." insert -- about --.

Signed and Sealed this

Eleventh Day of September 1979

[SEAL]

Attest:

Attesting Officer

LUTRELLE F. PARKER

Acting Commissioner of Patents and Trademarks